US00PP10677P

United States Patent [19]

Parsons

[11] Patent Number: Plant 10,677

[45] Date of Patent: Nov. 10, 1998

[54] PANDOREA PLANT NAMED 'SOUTHERN BELLE'

[76] Inventor: Rod Parsons, Falls Road, Hoddles Creek, Victoria 3139, Australia

[21] Appl. No.: 867,699

[22] Filed: Jun. 2, 1997

[51] Int. Cl.[6] ..... A01H 5/00

[52] U.S. Cl. ..... Plt./54.1

[58] Field of Search ..... Plt./54.1

[56] References Cited

PUBLICATIONS

GTITM UPOVROM Citation for 'Southern Belle' as per NZ PBRISHM 083, Apr. 14, 1996.

GTITM UPOVROM Citation for 'Southern Belle' as per AU PBR 95110, Feb. 28, 1997.

*Primary Examiner*—James R. Feyrer
*Assistant Examiner*—Kent L. Bell
*Attorney, Agent, or Firm*—C. A. Whealy

[57] ABSTRACT

A distinct cultivar of Pandorea plant named 'Southern Belle', characterized by its bright pink tubular flowers that face upward and outward; upright and outwardly arching, freely branching and dense plant habit; dark green leaves; early and continuous flowering during periods of warm temperatures; and numerous flowers per panicle.

1 Drawing Sheet

The present invention relates to a new and distinct cultivar of Pandorea plant botanically known as *Pandorea jasminoides,* and hereinafer referred to by the cultivar name 'Southern Belle'.

The new cultivar was selected by the inventor in 1991 from seedling progeny from unidentified parental selections of *Pandorea jasminoides* with the intent of selecting plants with a more attractive flower color, more and larger flowers, earlier flowering, and longer-lasting flowers.

The cultivar 'Southern Bell' was discovered and selected by the inventor as a flowering plant within the population of seedling progeny in a controlled environment in Hoddles Creek, Victoria, Australia. Asexual reproduction of the new cultivar by terminal cuttings taken at Hoddles Creek, Victoria, Australia, has shown that the unique features of this new Pandorea are stable and reproduced true to type in successive generations.

The cultivar 'Southern Belle' has not been observed under all possible environmental conditions. The phenotype may vary somewhat with variations in environment such as temerature and light intensity, without, however, any variance in genotype. The following observations, measurements and comparisions describe plants grown in Encinitas, Calif. during the winter and spring in a polyethylene-covered greenhouse with temperatures ranging from 18° to 26° C. and light levels of about 3,000 footcandles, and during the summer in Hoddles Creek, Victoria, Australia.

The following traits have been repeatedly observed and are determined to be the unique characteristics of 'Southern Belle'. These characteristics in combination distinguish 'Southern Belle' as a new and distinct cultivar:

1. Bright pink tubular flowers that face upward and outward.
2. Upright and outwardly arching, freely branching and dense plant habit.
3. Dark green leaves.
4. Early and continuous flowering during periods of warm temperatures.
5. Very floriferous with numerous flowers per panicle.

The cultivar 'Southern Belle' can be compared to the nonpatented *Pandorea jasminoides* cultivars 'Bower of Beauty' and 'Lady Di'. In side-by-side comparisions conducted at Hoddles Creek, Victoria, Australia, plants of the cultivar 'Southern Belle' have larger and more flowers, longer corolla tubes and wider petals. In addition, plants of the new cultivar have a darker pink petal color compared to plants of the cultivars 'Bower of Beauty' and 'lady Di'.

The accompanying colored photographs illustrate the overall appearance of the new cultivar, showing the colors as true as it is reasonably possible to obtain in colored reproductions of this type.

The first photograph comprises a top perspective view of a typical plant of the cultivar 'Southern Belle'.

The second photograph comprises a close-up view of individual flowers of the cultivar Southern Belle. Flower and foliage colors may appear different than the actual colors due to light reflectance.

In the following description, color references are made to The Royal Horticultural Society Colour Chart except where general terms of ordinary dictionary significance are used. Measurements are averages from six specimens selected at random.

Botanical classification: *Pandorea jasminoides* cultivar 'Southern Belle'.

Parentage:

*Male or pollen parent.*—Unidentified *Pandorea jasminoides* selection.

*Female or seed parent.*—Unidentified *Pandorea jasminoides* selection.

Propagation:

*Type cutting.*—Terminal vegetative cuttings.

*Time to initiate roots.*—About 21 days at 21° C. soil temperature.

*Rooting habit.*—Numerous, fine, fibrous, and well-branched.

Plant description:

*Form.*—Upright to outwardly arching shrub. Plants will climb if support is provided.

*Branching habit.*—Freely branching from base, bushy and dense.

*Plant height.*—About 20 1 cm.

*Vigor.*—Moderate.

*Foliage description.*—Leaves odd-pinnate with 5 to 7 leaflets, opposite. Size, terminal leaflet: Length: About 5.5 cm. Width: About 2.25 cm. Size, lateral leaflet: Length: About 4.75 cm. Width: About 1.75 cm. Shape: Oval to ovate. Aspect: Horizontal. Apex: Acute to aristate. Base: Attenuate. Margin: Entire.

Texture: Glabrous. Color: Young foliage upper side: 146A to 147A. Young foliage under side: 146A. Mature foliage upper side: 147A. Mature foliage under side: 147B.

*Stem description.*—Stems upright to outwardly arching. Stem diameter: About 3 mm. Internode length: About 3.5 cm. Stem color: 147A.

Flower description:

*Flower type and habit.*—Flowers arranged on terminal panicles and face upward and outward. Calyx five-parted, petals united into a flower tube. Flowers not persistent.

*Natural flowering season.*—Year-round in warm climates, in cooler climates, typically spring through fall.

*Quantity.*—Numerous flowers per panicle.

*Corolla.*—Diameter: About 7.5 cm. Height: About 7 cm. Flower tube width at distal end: About 1.5 cm. Flower tube length: About 4.5 cm. Petal quantity: Five, fused. Petal apex: Rounded. Margin: Rippled, Crenate. Texture: Velvety, pubescent. Color: Flower throat (inside): At base, whiskered and pale yellow, 11D, with purple, 59A, spots. Towards apex, 64B/67A. Flower tube color (outside): 75D. Petal color, inside: 68A/68B with lighter pink, 75B, towards margin. Color becomes lighter pink, 75B, with development. Petal color, outside: 75D.

*Sepals.*—Quantity: Five. Size: Length: About 8 mm. Width: About 3 mm. Shape: Fused, cup-shaped. Apex: Rounded. Margin: Entire. Texture: Smooth. Aspect: Upright. Color: Inside: White. Outside: Green at base, white at apex.

*Pedicel.*—Aspect: Upright or outward. Size: Length: About 1.5 cm. Width: About 1.5 mm. Texture: Smooth. Color: 146A.

*Reproductive organs.*—Stamens: Stamen number: Four. Anther color: White. Filament color: White. Pistils: Stigma color: White. Style color: White.

Disease resistance: No Known Pandorea diseases observed to date.

Seed production: Rearly observed.

It is claimed:

1. A new and distinct cultivar of Pandorea plant named 'Southern Belle', as illustrated and described.

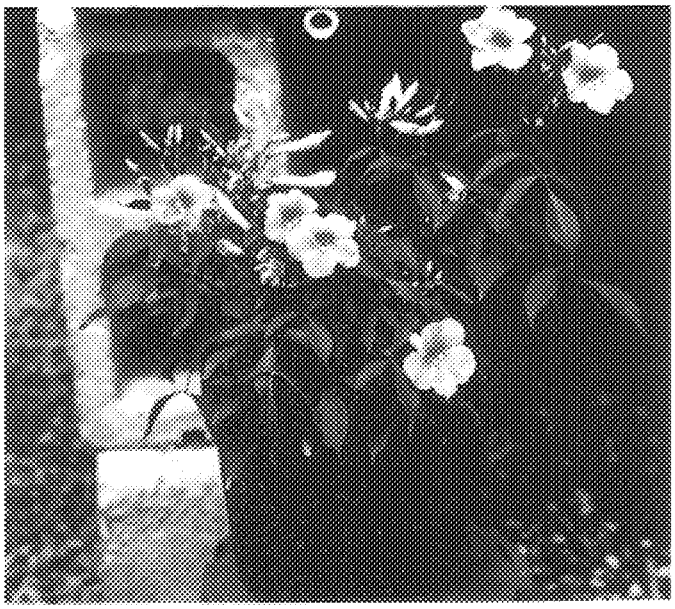
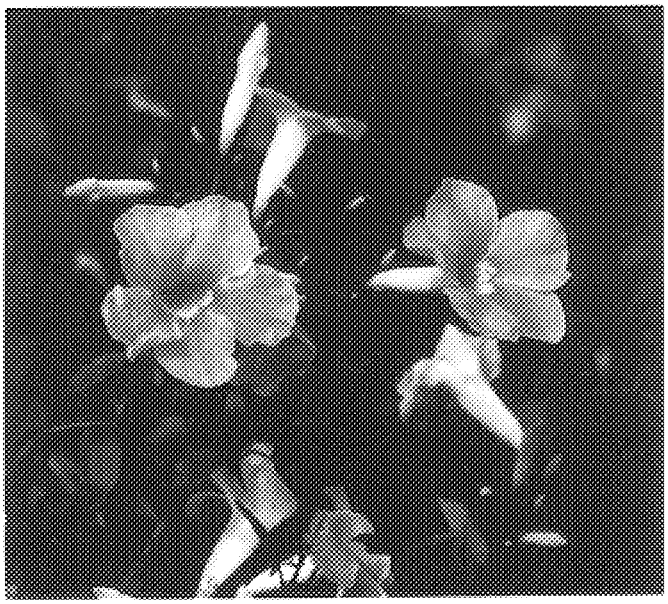

* * * * *